US011065188B2

(12) United States Patent
Zak et al.

(10) Patent No.: US 11,065,188 B2
(45) Date of Patent: Jul. 20, 2021

(54) APPLICATIONS AND FORMULATIONS OF OPTIMIZED, MODIFIED HUMAN EMBRYONIC FERTILITY CULTURE MEDIA WITH BIGUANIDES AND/OR FUNCTIONAL EQUIVALENTS

(71) Applicant: AV Laboratories LLC, N Redington Beach, FL (US)

(72) Inventors: Jan Zak, Wroclaw (PL); Ami Mezezi, New York, NY (US); Julian Pino, Branford, CT (US); Nildi Pino, Chicago, IL (US)

(73) Assignee: AV Laboratories LLC, N. Redington Beach, FL (US)

( * ) Notice: Subject to any disclaimer, the term of this patent is extended or adjusted under 35 U.S.C. 154(b) by 0 days.

(21) Appl. No.: 15/929,863

(22) Filed: May 26, 2020

(65) Prior Publication Data

US 2020/0375863 A1 Dec. 3, 2020

Related U.S. Application Data

(60) Provisional application No. 62/853,742, filed on May 29, 2019.

(51) Int. Cl.
*A61K 8/43* (2006.01)
*A61K 9/10* (2006.01)
(Continued)

(52) U.S. Cl.
CPC ............... *A61K 8/43* (2013.01); *A61K 8/498* (2013.01); *A61K 8/64* (2013.01); *A61K 8/676* (2013.01);
(Continued)

(58) Field of Classification Search
CPC ........ A61K 8/43; A61K 8/676; A61K 31/155; A61K 8/062; A61K 2800/91;
(Continued)

(56) References Cited

U.S. PATENT DOCUMENTS

| 5,719,050 A | 2/1998 | Makoto et al. |
| 8,361,485 B2 | 1/2013 | Naughton et al. |

(Continued)

FOREIGN PATENT DOCUMENTS

| CN | 105748518 B | 7/2016 |
| JP | 5885233 B2 | 12/2012 |

(Continued)

OTHER PUBLICATIONS

Bolnick et al. (J. Assist Reprod Genet 2016;33:1027-1039) (Year: 2016).*

(Continued)

*Primary Examiner* — Ernst V Arnold
(74) *Attorney, Agent, or Firm* — Halloran Sage LLP

(57) ABSTRACT

A dermatological preparation comprises an optimized, modified human embryonic fertility culture media with biguanides and/or functional equivalents and the use of said preparation for skin care, hair care, or body care, or dental procedures, or for regenerative medicine such as promoting wound or bone healing. The preparation is formulated to target the hypoxic microenvironment niches of the skin tissue in combination with optimal concentration of nutrients, ions and minerals; to stimulate existing stem cells to trigger the capacity of stem cells to divide and renew and differentiate into specialized cells; and to stimulate molecular and physiological processes, e.g., autophagy, to replenish the substrate pool through the recycling of organelles and the recycling of old damaged proteins and countering free-radical damage to promote anti-aging.

25 Claims, 20 Drawing Sheets

(51) Int. Cl.

| | | |
|---|---|---|
| *A61Q 19/00* | (2006.01) | |
| *A61K 8/19* | (2006.01) | |
| *A61K 8/49* | (2006.01) | |
| *A61K 31/353* | (2006.01) | |
| *A61K 8/64* | (2006.01) | |
| *A61K 38/05* | (2006.01) | |
| *A61K 38/08* | (2019.01) | |
| *A61K 8/67* | (2006.01) | |
| *A61K 31/375* | (2006.01) | |
| *A61K 31/155* | (2006.01) | |
| *A61K 9/00* | (2006.01) | |
| *A61K 9/107* | (2006.01) | |
| *A61K 9/113* | (2006.01) | |
| *A61K 8/06* | (2006.01) | |

(52) U.S. Cl.
CPC .......... *A61K 31/155* (2013.01); *A61K 31/353* (2013.01); *A61K 31/375* (2013.01); *A61K 38/05* (2013.01); *A61K 38/08* (2013.01); *A61K 8/062* (2013.01); *A61K 8/064* (2013.01); *A61K 8/066* (2013.01); *A61K 8/068* (2013.01); *A61K 9/0014* (2013.01); *A61K 9/0019* (2013.01); *A61K 9/0048* (2013.01); *A61K 9/1075* (2013.01); *A61K 9/113* (2013.01); *A61K 2800/91* (2013.01)

(58) Field of Classification Search
CPC .... A61K 31/353; A61K 31/375; A61K 38/05; A61K 38/08; A61K 8/064; A61K 8/066; A61K 8/068; A61K 8/19; A61K 8/20; A61K 8/24; A61K 8/36; A61K 8/365; A61K 8/44; A61K 8/442; A61K 8/447; A61K 8/4913; A61K 8/492; A61K 8/4946; A61K 8/498; A61K 8/60; A61K 8/64; A61K 9/0014; A61K 9/0019; A61K 9/0048; A61K 9/1075; A61K 9/113; A61Q 11/00; A61Q 19/00; A61Q 19/08; A61Q 5/00

See application file for complete search history.

(56) References Cited

U.S. PATENT DOCUMENTS

| | | | |
|---|---|---|---|
| 8,507,276 B2 | 8/2013 | Gohla et al. | |
| 2007/0041915 A1 | 2/2007 | Potier et al. | |
| 2009/0274732 A1* | 11/2009 | Hoffmann | A61P 3/10 424/400 |
| 2013/0059916 A1* | 3/2013 | Rocchi | A61P 3/10 514/635 |
| 2015/0342854 A1 | 12/2015 | Shibuya et al. | |
| 2016/0303281 A1 | 10/2016 | Salamone et al. | |

FOREIGN PATENT DOCUMENTS

| | | |
|---|---|---|
| WO | WO 2008/070368 A2 | 6/2008 |
| WO | WO 2017/187287 A1 | 11/2017 |
| WO | WO 2017/209658 A1 | 12/2017 |

OTHER PUBLICATIONS

Meindl et al. (Plos One 2015; 19 pages) (Year: 2015).*
Bolnick et al. (J Assist Reprod Genet 2017;34:1609-1617) (Year: 2017).*
Acetyl hexapeptide-8 [online] retrieved on Mar. 12, 2021 from: https://www.experchem.com/files/files/file/1fa5bfdc-83e3-4843-adb3-faa1ac020f62/Acetyl-hexapeptide-8-Productinformation-ExperChem.pdf; 2 pages. (Year: 2021).*
Summers, M., A brief History of the Development of the KSOM family of media, J. Assist Reprod Genet (2013) 30:995-999.
Qing, L et al., Metformin induces the M2 macrophage polarization to accelerate the wound healing via regulating AMPK/mTor/NLRP3.., Am J Transl Res 2019:11(2); 655-668.
Bedogni, B. et al., Hypoxia, melanocytes and melanoma—survival and tumor development in the permissive microenvironment of the skin. Pig.Cell Me. Res. (2009) 22; 166-174.
Yu, Y. et al., Metabolite availability as a window to view the early embryo microenvironment in vivo, Mol. Reprod, Dev. 2017:84; 1027-1038.
Kim, Y. et al., mTOR a pharmacologic target for autophagy regulation. J Clin Invest. 2015: 125(1)25-32.
Ji, J. et al., Aging in hair follicle stem cells and niche microenvironment. J Derm. 2017; 44(10): 1097-1104.
Rabinovitch, P., et al., Modulating mTOR in Aging and Health. Interdiscipl Top Gerontol. Basel, Karger. 2015; 40: 107-127.
Kazanci, A. et al., Analyses of changes on skin by aging. Skirt Research Tech. 2016: 0: 1-13.
Kruse, C. et. al., The external microenvironment of healing skin wounds. Wound Repair and Regeneration 2015: 23(4): 456-464.
McDaniel, D. et al., Atmospheric skin aging Contributors and inhibitors. J. Cosmet Dermatol. 2018;17:124-137.
Mossmann, D., et al., mTOR Signaling and cellular metabolism are mutual determinants in cancer. Nature Reviews Cancer. 2018; 18: 744-757.
Perluigi, M., et al., mTOR Signaling in aging and neurodegeneration: At the crossroad between metabolism dysfunction and impairment of autophagy. Neurobiology of Disease.
Salamonsen, L., et al., The Microenvironment of Human Implantation: Determinant of Reproductive Success. Am. J. of Reprod. Immuno. 2016; 75: 218-225.
Scalise, A. et al., Microenvironment and Microbiology of Skin Wounds: The Role of Bacterial Biofilms and Related Factors. Semin. Vasc. Surg. 2015; 28: (3-4): 151-159.
Shimizu, I., et al., DNA Damage Response and Metabolic Disease, Cell Metabolism 2014: 20(6): 967-977.
Wells, A., et al., Skin Tissue repair: Matrix microenvironmental influences. Matrix Biology 2016: 49: 25-36.
International Search Report and Written Opinion for Application No. PCT/US2020/070077, dated Jan. 15, 2021.
No Author Listed, Acetyl_hexapeptide-3. Wikipedia. Aug. 8, 2018; 3 pages. https://en.wikipedia.org/w/index.php?title=Acetyl_hexapeptide-3&oldid=863095429 'Acetyl 25/hexapeptide-3'. Last accessed Sep. 23, 2020.
Van Aller et al., Epigallocatechin gallate (EGCG), a major component of green tea, is a dual phosphoinositide-3-kinase/mTOR inhibitor. Biochem Biophys Res Commun. Mar. 11, 2011;406(2):194-9. doi: 10.1016/j.bbrc.2011.02.010. Epub Feb. 15, 2011.

* cited by examiner

FIG. 1.

| Substrate | Concentration range [g/L] | |
|---|---:|---:|
| NaCl | 4.44 | 11.1 |
| KCl | 0.152 | 0.38 |
| KH2PO4 | 0.04 | 0.1 |
| MgSO4·7H2O | 0.04 | 0.1 |
| Glucose | 0.032 | 0.08 |
| Sodium lactate | 0.896 | 2.24 |
| NaHCO3 | 1.68 | 4.2 |
| Sodium pyruvate | 0.016 | 0.04 |
| CaCl2·2H2O | 0.02 | 0.05 |
| EDTA | 0.0032 | 0.008 |
| Glycyl-glutamine | 0.1168 | 0.292 |
| L-Glutamine | 0.008 | 0.02 |
| L-Alanine | 0.0036 | 0.009 |
| Glycine | 0.003 | 0.0075 |
| L-Arginine | 0.05056 | 0.1264 |
| L-Asparagine | 0.006 | 0.015 |
| L-Aspartic Acid | 0.005328 | 0.01332 |
| L-Cystine | 0.009616 | 0.02404 |
| L-Histidine | 0.016768 | 0.04192 |
| L-Isoleucine | 0.020984 | 0.05246 |
| L-Leucine | 0.020992 | 0.05248 |
| L-Lysine | 0.029216 | 0.07304 |
| L-Methionine | 0.005968 | 0.01492 |
| L-Phenylalanine | 0.013216 | 0.03304 |
| L-Proline | 0.004608 | 0.01152 |
| L-Serine | 0.004208 | 0.01052 |
| L-Tryptophan | 0.004088 | 0.01022 |
| L-Tyrosine | 0.014496 | 0.03624 |
| L-Valine | 0.018736 | 0.04684 |

FIG 2.

| Substrate | Optimal Concentration |
|---|---|
| NaCl | 5.55 g/L |
| KCl | 0.19 g/L |
| KH2PO4 | 0.05 g/L |
| MgSO4·7H2O | 0.05 g/L |
| Glucose | 0.04 g/L |
| Sodium lactate | 1.12 g/L |
| NaHCO3 | 2.1 g/L |
| Sodium pyruvate | 0.02 g/L |
| CaCl2·2H2O | 0.25 g/L |
| EDTA | 0.004 g/L |
| Glycyl-glutamine | 0.146 g/L |
| L-Glutamine | 0.01 g/L |
| L-Alanine | 0.0045 g/L |
| Glycine | 0.00375 g/L |
| L-Arginine | 0.0632 g/L |
| L-Asparagine | 0.0075 g/L |
| L-Aspartic Acid | 0.00666 g/L |
| L-Cystine | 0.01202 g/L |
| L-Histidine | 0.02096 g/L |
| L-Isoleucine | 0.02623 g/L |
| L-Leucine | 0.02624 g/L |
| L-Lysine | 0.03652 g/L |
| L-Methionine | 0.00746 g/L |
| L-Phenylalanine | 0.01652 g/L |
| L-Proline | 0.00576 g/L |
| L-Serine | 0.00526 g/L |
| L-Tryptophan | 0.00511 g/L |
| L-Tyrosine | 0.01812 g/L |
| L-Valine | 0.02342 g/L |
| Biguanide | 0.1-10 g/L |

FIG. 3.

| Substrate | % by weight (range) | |
|---|---|---|
| LaSecret Formula™ | 10 | 70 |
| Dimethicone | 3.33 | 10 |
| Cyclomethicone | 1.998 | 6 |
| Glycerin | 1.998 | 6 |
| Paraffinum liquidum | 1.332 | 4 |
| Antioxidant complex | 1.332 | 4 |
| Aloe barbadensis | 1.332 | 4 |
| Cetyl alcohol | 1.332 | 4 |
| Glyceryl stearate | 1.332 | 4 |
| Isohexadecane | 0.666 | 2 |
| Sodium lauryl phosphate | 0.999 | 3 |
| Malus pumila seed oil | 0.666 | 2 |
| Cocos nucifera oil | 0.666 | 2 |
| Rosa rubiginosa seed oil | 0.666 | 2 |
| Persea americana butter | 0.666 | 2 |
| Mangifera indica butter | 0.666 | 2 |
| Urea | 0.666 | 2 |
| PEG-40 castor oil | 0.333 | 1 |
| Simmondsia chinensis oil | 0.333 | 1 |
| Isopropyl myristate | 0.333 | 1 |
| Phenoxyethanol - Ethylhexylglycerin | 0.333 | 1 |
| Corylus avellana oil | 0.333 | 1 |
| Vitellaria paradoxa butter | 0.333 | 1 |
| Polysorbate 60 | 0.333 | 1 |
| EMT Polymer | 0.333 | 1 |
| Octyldodecanol | 0.333 | 1 |
| Allantoin | 0.333 | 1 |
| Theobroma grandiflorum butter | 0.0666 | 0.2 |
| Sodium L-pyroglutamate | 0.0666 | 0.2 |
| Hydroxycellulose | 0.0666 | 0.2 |
| Squalane | 0.0666 | 0.2 |
| Cera alba | 0.0666 | 0.2 |
| Ethylenediaminetetraacetic acid | 0.1332 | 0.4 |
| Coenzyme Q10 | 0.0666 | 0.2 |

FIG. 3 (Continue)

| Camellia sinensis extract | 0.0666 | 0.2 |
|---|---|---|
| Ascorbic acid | 0.0666 | 0.2 |
| Niacinamide | 0.0666 | 0.2 |
| Cyanocobalamin | 0.0666 | 0.2 |
| Cuprum | 0.0666 | 0.2 |

FIG. 4.

| Substrate | % by weight (range) | |
|---|---|---|
| LaSecret Formula™ | 10 | 70 |
| Rosa Damascena floral water | 3.33 | 10 |
| Argireline | 2.664 | 8 |
| Dimethicone | 2.664 | 8 |
| Glycerin | 1.998 | 6 |
| Isohexadecane | 1.998 | 6 |
| Royal jelly | 1.998 | 6 |
| Paraffinum liquidum | 1.998 | 6 |
| Cyclomethicone | 1.998 | 6 |
| Aloe vera | 1.332 | 4 |
| Petrolatum | 1.332 | 4 |
| Glyceryl stearate | 1.332 | 4 |
| Sodium lauryl phosphate | 0.999 | 3 |
| Propylene glycol | 0.666 | 2 |
| Rosa Rubiginosa seed oil | 0.666 | 2 |
| Prunus dulcis oil | 0.666 | 2 |
| Corylus avellana oil | 0.666 | 2 |
| Sodium acrylate / sodium acryloyldimethyl taurate copolymer, isohexadecane, polysorbate 80 mix | 0.666 | 2 |
| PEG-40 | 0.666 | 2 |
| Polysorbate 20 | 0.333 | 1 |
| Phenoxyethanol | 0.333 | 1 |
| Squalane | 0.666 | 2 |
| Allantoin | 0.333 | 1 |
| Cholesterol | 0.333 | 1 |
| Octyldodecanol | 0.333 | 1 |
| Urea | 0.333 | 1 |
| D-panthenol | 0.333 | 1 |
| Alpha-arbutin | 0.333 | 1 |
| Decyl glucoside | 0.333 | 1 |
| Silk amino acids | 0.0666 | 0.2 |
| Ascorbic acid | 0.333 | 1 |
| Hyaluronic acid | 0.0666 | 0.2 |
| Tocopherol | 0.0666 | 0.2 |

FIG. 4 (Continue)

| Ethylenediaminetetraacetic acid | 0.1332 | 0.4 |
|---|---|---|
| Cyanocobalamin | 0.0666 | 0.2 |
| Copper gluconate | 0.0666 | 0.2 |
| Zinc gluconate | 0.0666 | 0.2 |
| Cucumis sativus extract | 0.0666 | 0.2 |
| Vitellaria paradoxa butter | 0.0666 | 0.2 |
| Niacinamide | 0.0666 | 0.2 |
| Calcium gluconate | 0.0666 | 0.2 |

FIG. 5.

| Substrate | % by weight (range) | |
|---|---|---|
| LaSecret Formula™ | 10 | 70 |
| Aloe vera water | 4.329 | 10 |
| Dimethicone | 10.656 | 20 |
| Bifida ferment lysate | 3.33 | 10 |
| Sea kelp ferment | 3.33 | 10 |
| Glycerin | 1.998 | 6 |
| Glyceryl stearate | 2.331 | 7 |
| Cetyl alcohol | 1.332 | 4 |
| Apple seed oil | 0.666 | 2 |
| Rosehip seed oil | 0.666 | 2 |
| Hamamelis Virginiana extract | 0.666 | 2 |
| Argireline | 0.666 | 2 |
| Phenoxyethanol | 0.7992 | 2.4 |
| Mangifera indica butter | 0.5994 | 1.8 |
| Almond oil | 0.3996 | 1.2 |
| Jojoba oil | 0.333 | 1 |
| Butyrospermum parkii butter | 0.333 | 1 |
| Sambucus nigra fruit extract | 0.333 | 1 |
| Coenzyme Q10 | 0.0333 | 0.1 |
| Hialuronic acid | 0.3663 | 1.1 |
| Avocado butter | 0.333 | 1 |
| Polysorbate 60 wax | 0.333 | 1 |
| PEG-40 | 0.2997 | 0.9 |
| Polyglyceryl 6 dioleate, Sorbitan laurate, Dilautyl citrate mix | 0.666 | 2 |

FIG. 5 (Continue)

| Ascorbic acid | 0.666 | 2 |
|---|---|---|
| Urea | 0.666 | 2 |
| Caffeine | 0.0666 | 0.2 |
| Disodium EDTA | 0.0666 | 0.2 |
| Royal Jelly | 0.0999 | 0.3 |
| Hydroxycitranellal | 0.0333 | 0.1 |
| Linalool | 0.0333 | 0.1 |
| Fragrance | 0.0333 | 0.1 |

FIG. 6

| Substrate | % by weight (range) | |
|---|---|---|
| LaSecret Formula™ | 10 | 70 |
| Aloe Vera water | 3.33 | 10 |
| Glycerin | 1.998 | 6 |
| Bifida ferment lysate | 3.33 | 10 |
| Sea kelp ferment | 3.33 | 10 |
| Butylene Glycol | 1.998 | 6 |
| Sodium hyaluronate | 0.333 | 1 |
| Urea | 0.666 | 2 |
| Sambucus nigra fruit extract | 0.333 | 1 |
| Behenyl alcohol | 0.1332 | 0.4 |
| Hordeum vulgare extract | 0.1998 | 0.6 |
| Octyldodecanol | 0.666 | 2 |
| Phenoxyethanol | 0.666 | 2 |
| Acidum ascorbicum | 0.666 | 2 |
| Hydroxycitronellol | 0.0333 | 0.1 |
| Limonene | 0.0333 | 0.1 |
| Linalool | 0.0333 | 0.1 |
| Fragrance | 0.0333 | 0.1 |
| Xanthan gum | 0.999 | 3 |
| Coumarin | 0.0333 | 0.1 |
| D-panthenol | 0.666 | 2 |

FIG 7.

| Substrate | % by weight (range) | |
|---|---|---|
| LaSecret Formula™ | 10 | 95 |
| Rosa damascena water | 1.998 | 6 |
| Glycerin | 1.332 | 4 |
| Aloe vera extract | 1.332 | 4 |
| Butylene glycol | 0.666 | 2 |
| Acidum ascorbicum | 0.333 | 1 |
| Gluconolactone | 0.00666 | 0.02 |
| Punica granatum fruit extract | 0.00666 | 0.02 |
| Selenium | 0.0333 | 0.1 |
| Sodium hyaluronate | 0.1332 | 0.4 |
| Isohexadecane | 0.999 | 3 |
| Caffeine | 0.0333 | 0.1 |
| Cyanocobalamin | 0.01665 | 0.05 |
| Phenoxyethanol / Ethylhexyl glycerin | 0.666 | 2 |
| Disodium EDTA | 0.0333 | 0.1 |
| Hordeum vulgare extract | 0.0666 | 0.2 |
| Coumarin | 0.0333 | 0.1 |
| Fragrance | 0.0333 | 0.1 |
| Hydroxycitronellol | 0.0333 | 0.1 |

FIG 8.

| Substrate | % weight (range) | |
|---|---|---|
| LaSecret Formula™ | 10 | 60 |
| Sodium Laureth Sulfate | 13.32 | 40 |
| Pyrus Malus fruit extract | 1.998 | 6 |
| Coco-glucoside | 6.66 | 20 |
| Glycerin | 1.332 | 4 |
| Gluconolactone | 2.664 | 8 |
| Wheat amino acids | 0.333 | 1 |
| Dimethicone | 0.666 | 2 |
| Propylene glycol | 0.666 | 2 |
| Phenoxyethanol | 0.4662 | 1.4 |
| Citric acid | 0.02664 | 0.08 |
| Disodium EDTA | 0.0666 | 0.2 |
| Fragnance | 0.05328 | 0.16 |
| Propanediol | 0.999 | 3 |
| Glycol Distearate | 0.1332 | 0.4 |
| Laureth-4 | 0.1332 | 0.4 |
| Potassium sorbate | 0.1332 | 0.4 |
| Sodium benzoate | 0.2664 | 0.8 |
| Hydroxycitronellal | 0.0333 | 0.1 |
| Linalool | 0.0333 | 0.1 |

FIG. 9.

| Substrate | % weight (range) | |
|---|---|---|
| LaSecret Formula™ | 10 | 85 |
| Glycerin | 1.998 | 6 |
| Cetyl alcohol | 1.332 | 4 |
| Aloe Vera leaf juice | 1.998 | 6 |
| Apple seed oil | 0.2664 | 0.8 |
| Coconut oil | 0.2664 | 0.8 |
| Rosehip seed oil | 0.1332 | 0.4 |
| Wheat amino acids | 0.1665 | 0.5 |
| Glyceryl stearate | 2.331 | 7 |
| Cetyl esters | 0.333 | 1 |
| Potassium sorbate | 0.333 | 1 |
| Citric acid | 0.0666 | 0.2 |
| Sodium benzoate | 0.2664 | 0.8 |
| Salicylic acid | 0.0666 | 0.2 |
| Hydroxycitronellal | 0.0333 | 0.1 |
| Linalool | 0.0333 | 0.1 |
| Fragrance | 0.0333 | 0.1 |
| Tocopherol | 0.04662 | 0.14 |
| Mica | 0.0666 | 0.2 |
| Guar gum | 0.0666 | 0.2 |

FIG. 10.

| Substrate | % weight (range) | |
|---|---|---|
| LaSecret Formula™ | 10 | 70 |
| Aloe Vera juice | 3.33 | 10 |
| Glycerin | 2.331 | 7 |
| Cetyl alcohol | 1.332 | 4 |
| Dimethicone | 3.33 | 10 |
| Urea | 0.666 | 2 |
| Coenzyme Q10 | 0.01665 | 0.05 |
| Avocado Butter | 2.664 | 8 |
| Acidum ascorbicum | 0.666 | 2 |
| Argireline | 0.999 | 3 |
| Sambucus Nigra flower extract | 0.1332 | 0.4 |
| Acerola ferment | 0.15984 | 0.48 |
| Bifida ferment lysate | 3.33 | 10 |
| Tocopherol | 0.04662 | 0.14 |
| Hyaluronic acid | 0.4329 | 1.3 |
| Sea Kelp ferment | 1.332 | 4 |
| Behenyl alcohol | 1.332 | 4 |
| Prunus Amygdalus Dulcis seed extract | 0.2664 | 0.8 |
| Caffeine | 0.04329 | 0.13 |
| Phenoxyethanol & Ethylhexylglycerin | 0.7992 | 2.4 |
| Wheat amino acids | 0.333 | 1 |
| Guar gum | 0.999 | 3 |
| Coumarin | 0.04329 | 0.13 |
| Hydroxycitronellal | 0.0333 | 0.1 |

FIG. 10 (Continue)

| Linalool | 0.0333 | 0.1 |
|---|---|---|
| Fragrance | 0.0333 | 0.1 |

FIG. 11.

| Substrate | % weight (range) | |
|---|---:|---:|
| 96% Ethyl alcohol | 29.97 | 90 |
| Isopropyl alcohol | 18.648 | 56 |
| LaSecret Formula™ | 10.59273 | 31.81 |
| Aloe vera juice | 6.66 | 20 |
| Benzyl alcohol | 0.666 | 2 |
| Tocopherol | 0.06327 | 0.19 |

FIG. 12.

| Substrate | % weight (range) | |
|---|---|---|
| LaSecret Formula™ | 80 | 99.9 |
| Niacinamide | 0.3 | 0.5 |
| Hyaluronic acid | 0.3 | 1 |
| Hexapeptide-8 (argireline) | 0.3 | 10 |

\*   $p < 0.05$
\*\*  $p < 0.01$
\*\*\* $p < 0.001$
ns  Not Statistically Significant \* $p < 0.05$
\*\* $p < 0.01$
\*\*\* $p < 0.001$
ns  Not Statistically Significant a.

Selecting a first media, defining a "START" simplex;

Identifying the composition of said first media including osmolarity, pH, nutrients, preservatives, and energy substrates, e.g., glucose and TCA intermediates;

Dissecting "START" simplex into essential and non-essential components;

Selecting a "TARGET" location, e.g., skin tissue, conjunctiva, wound, or dental procedures;

Identifying the specific characteristics of the microenvironment niche of "TARGET" location including osmolarity, pH, commensal and non-commensal microorganisms, and other physiological characteristics;

Dissecting the "TARGET" location into essential and non-essential parameters in terms of microenvironment, metabolic demands, physiology, and microbial abundance;

Cross-comparing the essential, non-essential substances as well as characteristics, keeping in mind potential negative substrate-substrate interactions between the "START" simplex as well as "TARGET" location;

Identifying target components for optimization in the new media, e.g., EDTA, NaCl, Pyr, $KH_2PO_4$, Glucose, and other desirable components;

 Modifying and optimizing the formulation until the desired and optimal composition is achieved. 

APPLICATIONS AND FORMULATIONS OF OPTIMIZED, MODIFIED HUMAN EMBRYONIC FERTILITY CULTURE MEDIA WITH BIGUANIDES AND/OR FUNCTIONAL EQUIVALENTS

CROSS-REFERENCE TO RELATED APPLICATIONS

The present application claims priority under 35 U.S.C. § 119(e) of U.S. Provisional Application No. 62/853,742, filed on May 29, 2019, entitled "Novel Applications and formulations of Modified Human Embryonic Fertility Culture Media and/or their derivatives combined with biguanides and/or Functional derivatives."

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATED-BY-REFERENCE OF MATERIAL SUBMITTED ON COMPACT DISC OR AS A TEXT FILE VIA THE OFFICE ELECTRONIC FILING SYSTEM (EFS-WEB)

Not Applicable

STATEMENT REGARDING PRIOR DISCLOSURE BY THE INVENTOR OR A JOINT INVENTOR

Not Applicable

BACKGROUND OF THE INVENTION

1. Field of the Invention

The present invention relates to a dermatological preparation comprising optimized, modified human embryonic fertility culture media with biguanide and/or functional equivalents and/or essential metabolic substrates and the use of said preparation in topical, injectable or depot formulation for skin care, hair care, body care, dental procedures, and for anti-aging and regenerative medicine such as promoting wound or bone healing. The present invention further relates to a method for preparing optimized modified human embryonic fertility culture media for skin care, hair care, body care, dental procedures, and for anti-aging and regenerative medicine such as promoting wound or bone healing.

2. Description of Related Art

Patients may present with any number of skin conditions. Some common complications include burns, hyper-pigmentation, scarring, bleeding, hematoma, bruises, rashes or other manifestations of allergic reactions, angioedema, or eyelid or eyebrow ptosis, drooping, and various types of skin cancer.

Exposure to UV radiation from the sun can cause a variety of reversible and irreversible skin changes. These changes range from healthy tanning, mild rashes to more severe cases such as adverse immunologic response that leads to the development of anaphylaxis. Chronic UV light exposure can also cause premature aging of the skin ("photoaged skin") which results in rough, dyspigmented lesions and the increased appearance of both fine and deep wrinkles.

In relation to the aging process, the skin poses a great challenge. Since the skin is the largest and most exposed human organ, any signs of aging are immediately apparent. Herein, we define skin aging as a complex process that involves intrinsic and extrinsic factors that cause a progressive impairment of the skin's ability to maintain homeostasis. Accumulated DNA damage as well as shortened telomere length in biologically older skin has limited ability to respond to oxidative stress. This limits the skin's ability to regenerate extracellular as well as intracellular proteins such as collagen and elastin.

The overall phenotypic effect of "intrinsic aging" of the skin produces lines, wrinkles, age spots, splotches, dyspigmentation, dull skin texture, and other skin flaws. Premature aging of the skin may also occur through external insults from exposure to harmful agents such as UV radiation from natural or artificial sunlight ("photoaged skin"), including exposure to UV radiation from tanning beds. In cases where the diet is poor in antioxidants, the effects of both extrinsic and intrinsic causes of aging are magnified.

It is known in the art that numerous aging processes can be targeted by nutritional, genetic, pharmacologic and surgical interventions to enhance and extend health and longevity in experimental animal models. Generally, the molecular and physiological processes underlying the biology of aging include DNA damage, telomere shortening, metabolism, proteostasis, macromolecular damage, inflammation, adaptation to stress, epigenetics, and stem cells and their renewal ability.

Similarly, the biological causes of skin aging ("intrinsic aging" or "natural aging process") include oxidative respiration, the accumulation of genetic mutations, telomere shortening, epigenetics of aging, unfolded protein response (UPR), mitochondrial dysfunction, cellular senescence, inflammation, and stem cell exhaustion.

In terms of metabolism, the inverse correlation between lifetime exposure to insulin and aging (i.e., longevity) is well established. Lower insulin correlates with increased lifespan across a wide range of animal models. These results highlight the importance of the metabolic component of aging arising from within cells. A proposed mechanism explaining this phenomenon is the decreased endogenous free-radicals production through decreased mitochondrial oxidative respiration. A similar correlation with insulin has been observed in patients with insulin resistant type II diabetes mellitus (DMII). DMII patients have chronic elevated insulin levels with decreased glucose tolerance and increased markers of aging. These clinical effects include increased incidence of heart and cerebrovascular disease, obesity, hypertension and the complications associated with these conditions including cancer and impaired wound healing. The aforementioned diseases increase mortality and morbidity.

High glucose concentrations in the blood are neurotoxic. Damaged nerves impair wound repair where even a small cut may result in a loss-of-limb infection. A common primary intervention in patients with impaired glucose tolerance (mild DMII), is the use of biguanides such as oral metformin. It is known that patients taking metformin live longer. The precise mechanism by which this occurs is not fully understood; however, it is hypothesized that metformin normalizes blood glucose levels and improves insulin sensitivity. A means for regulating blood glucose levels is desired to control the aging process.

The skin is the largest organ of the body. The epidermis forms the outermost layer of the skin and thus is an important target for cosmetic or medical intervention.

Furthermore, the epidermis comprises five (5) layers: *S. basale, S. spinosum, S. granulosum, S. lucidum, S. corneum*. The most metabolically active and deepest layer of the five layers is the *stratum basale* (*S. basale*). Within this deepest layer and the greatest distance from the skin surface, *S basale* of the epidermis contains actively dividing stem cells.

The prior art including present cosmetic or medical interventions do not take into consideration the microenvironment in which the epidermis exists and the opportunities and challenges for intervention it presents. Knowledge and understanding of the epidermal/dermal microenvironment may help in designing protocols for intervention that support the microenvironment present in skin tissue to promote tissue regeneration, anti-aging, and overall skin health.

Specifically, for instance, like the microenvironment in which early embryos exist, the epidermis exists in an avascular hypoxic (low oxygen) environment. This hypoxic environment is further exacerbated by the colonization of commensal bacteria and other microorganisms on the skin. Since the diffusion ability of oxygen is less than 300 μm, there is insufficient oxygenation of the epidermis from the external environment. Furthermore, any oxygen present from the surrounding atmosphere is quickly used up by commensal bacteria and other microorganisms that colonize the skin.

The prior art including present cosmetic or dermatological preparations, or medical interventions also fail to appreciate the remarkable, biological properties of stem cells including, inter alia, the capacity of stem cells to divide and renew themselves and, under certain physiologic conditions, the capacity of stem cells to become specialized cell types including specialized cells that form the skin—keratinocytes, melanocytes, Merkel cells, and Langerhans cells. There are many treatment options available for treating skin conditions, but all these treatment options overlook the significance of defining and controlling the composition of the microenvironment niches within the skin tissue that regulate and influence the biological properties of stem cells.

Another limitation with present cosmetic products—particularly products purporting anti-aging, or skin "revitalizing," or "rejuvenating" properties—is that consumers are presented with a broad choice of available products with only limited data regarding their efficacy.

A further limitation of the prior art and present cosmetic anti-aging products is the narrow focus on countering free radicals. These products are rich in free-radical scavengers (e.g., vitamin C, vitamin E, Coenzyme Q10, and idebenone) that may help to slow the aging process but there is little evidence that they offer any additional benefits.

A further limitation of the prior art and present cosmetic anti-aging products is the adverse and antagonist effects of these products on the natural aging process. It would be highly advantageous to develop a cosmetic anti-aging formulation that works in synergy with the skin's natural biology and supports a favorable microenvironment to restore the gene expression profile of youthful cells. Biguanides have been shown in vitro and in vivo to alter the gene expression profile of older cells to resemble the expression profile of younger cells, and, as discussed previously, biguanides such as oral metformin normalizes blood glucose levels and improves insulin sensitivity In yet another limitation of the prior art and present cosmetic anti-aging products is the dependence on exogenous administration of growth factors, peptides, sera, cytokines, and other bioeffectors that offer only transitory benefits. It is known in the art that upon removal of these stimulating bioeffectors, stimulated cells revert to the unstimulated, starved state.

In yet another limitation of the prior art, prior formulations comprise a blindly mixed composition of substrates, extracts, vitamins, oils, essential oils, fermentation products, and other non-specific ingredients that are not necessarily compatible and may have countervailing properties. For example, as the substrate compositions becomes more complex, the number of potential substrate-substrate interactions increases proportionately. A substrate designed to stimulate growth, regeneration and/or repair may be perturbed or its effects may be reversed by other substrate(s) in the formulation. The beneficial properties of one substrate may be countered by the presence of another substrate.

It would be highly desirable to use a synergistic combination of specific substrates and optimized, human embryonic fertility media conditions in a formulation to provide nourishment to the skin as well as promote anti-aging, tissue regeneration, wound and bone healing, and general good health. The formulation comprising optimized concentrations of substrates (nutrients, minerals, peptides, essential and non-essential amino acids, and other substrates) and media conditions (pH and osmolarity) that target the often hypoxic microenvironment niche of the skin tissue and that stimulate the existing stem cells of *S basale* layer as well as stromal cells in the epidermal/dermal junction.

In yet another limitation of the prior art, few methods contemplate the use of culture media in cosmetic or dermatological products for the skin to promote anti-aging and/or regenerative properties of the skin. Present methods employing the use of culture media contemplate the use of tissue culture media designed and specifically optimized for somatic cells but fail to optimize media conditions for the microenvironment niches within the skin tissue that regulate and influence the biological properties of stem cells. There are no known methods which contemplate the use of modified human embryonic fertility media in cosmetic or dermatological products for skin care, hair care, or body care, dental procedures, or for regenerative medicine such as wound or bone healing or for improving overall general health in the form of oral supplementation.

In yet another limitation of the prior art, present methods for creating fertility culture media with the preferred combination of substrate compositions seek to replicate culture conditions found in uterine fluids within the womb by measuring average substrate concentrations rather than the more preferable approach of capturing the dynamic microenvironment that supports embryonic growth during all stages of development. Present methods offer no proof of efficacy; are grossly inadequate; and identifying the preferred combination of substrate compositions is performed through trial-and-error with no systematic and rational methodology. Furthermore, measuring the effects of currently available fertility media on the success rate of embryonic implantation is controversial and further complicated by the use of growth-factors that inhibit apoptosis such as IGF-1. The long-term health effects on children born using IVF procedures employing current fertility media remains unknown.

Accordingly, it would further be highly desirable to employ methodical optimization to create a superior fertility media that comprises mathematically optimized substrate and solute compositions for the microenvironment niches within the skin tissue. Specifically, it would further be highly desirable to use optimized, human embryonic fertility media in combination with biguanides and/or functional derivatives and/or essential metabolic substrates to allow for direct application and incorporation into a cosmetic formulation. Since human embryonic culture medium contains all the necessary substrates to create a de novo human, its use as a stand-alone component of said cosmetic formulation is contemplated, described, and taught in the present invention. It is further contemplated that obvious modifications of the present invention includes, but is not limited to, the potential to supplement the preparation of the present invention with other beneficial components such as sera, inorganic phosphate, growth factors, cytokines, peptides and other bioactive molecules.

It would further be highly desirable to use optimized, human embryonic fertility media in formulations for use in topical, injectable or depot formulation for skin care, hair care, or body care, dental procedures, or for regenerative medicine that can produce clinically significant improvements in the appearance, vitality, and health of the skin.

To this end, commercial products designed for human fertility medicine offer unprecedented opportunities to develop novel applications in other fields that deal with similar challenges. Fields that may benefit from fertility medicine include, but not limited to, cosmetology, dermatology as well as surgery and anti-aging medicine.

It is known in the art that the developing human embryo and the epidermis exist in the same microenvironment and share renewal abilities due to the presence of stem cells. The early embryo is metabolically active prior to implantation and prior to the development of vasculature and, therefore, exists in an avascular hypoxic microenvironment. The epidermis also exists in an avascular hypoxic microenvironment and the presence of hypoxia in the epidermis is known in the art. The early embryo has omnipotent stem cells similar to the stem cells present in the *stratum basale* of the epidermis.

For cells to survive in avascular ischemic microenvironments they need to fuel their tri-carboxylic acid (TCA) cycle with other substrates. These substrates are either TCA intermediates or intermediates easily interchangeable with TCA intermediates via transamination reactions. The reason for this requirement is because they are unable to use oxygen as the final electron acceptor in the electron transport chain. Alternatively, anaerobic glycolysis will lead to acidosis, lactic acid build-up, and a low ATP yield per glucose molecule. Hence, cell survival is dependent on the maintenance of a proper metabolic substrate pool.

Cells can achieve an adequate substrate pool and prolong survival through a catabolic process known as autophagy, which is a process that recycles intracellular organelles. Cells that fail to maintain their substrate pool or exhaust their intracellular recycling potential, lose the ability to carry out enzymatic reactions and may undergo cell senescence or cell death. Accordingly, successful human in vitro fertilization requires the developing zygote to be surrounded with the optimal concentration of nutritional and energy substrates within its microenvironment including, but not limited to, nutrients, ions and minerals.

The significance of this is known in the art as zygotes cultured in saline arrest at the two-cell stage. More importantly, any perturbation in the surrounding environment of the zygote will be amplified logarithmically in the form of miscarriage, spontaneous abortion, or congenital defects. Hence, the zygote is the de facto most sensitive cell in the human and demand an enriched microenvironment to satisfy its evolving nutritional and energy requirements for specific nutrient and energy substrates.

In addition, fertilization of the ovum as well as the first cell divisions occur in the ampulla of the fallopian tube which, a priori, is a location that is an avascular hypoxic environment where the early embryo must utilize pre-formed RNA, and proteins formed prior to ovulation as well as metabolic substrates present in the fallopian tube fluid. Without an outside source of metabolic substrates, the developing zygote quickly expends its internal energy reservoir and ceases to divide. Low abundance of oxygen ($O_2$) prevents early embryonic metabolism relying on oxygen as the final electron acceptor. Alternatively, reliance on glycolysis alone will lead to acidosis. Proper embryonic metabolism in these initial stages must rely on the incorporation of various alternative substrates into the TCA cycle.

In this regard, healthy zygote development requires an enriched microenvironment which allows for (1) de novo synthesis of all non-essential amino acids and key substrates required for protein synthesis; (2) the generation of ATP; and (3) the promotion of important metabolic reactions. Healthy skin tissue also requires an optimized microenvironment.

The main function of the epidermis is to protect the body from the external environment—more precisely: pathogens, and toxins. The epidermis also helps maintain fluid homeostasis via the regulation of trans-epidermal fluid loss. There is no blood supply to the epidermis, and the diffusion of oxygen from surrounding air is insufficient to facilitate oxidative respiration. Unlike the sterile environment of the mother's womb, human skin is littered with commensal and non-commensal organisms including, but not limited to, *Streptococcus epidermidis, Staphylococcus aureus*, and *Candida albicans*. The result is a harsh microenvironment as cells must compete for any available oxygen with commensal and non-commensal bacteria and other microorganisms. Hypoxia staining (pimonidazole, EF5 etc.) all confirm the presence of hypoxia in the epidermis.

The dermis sits between the epidermis and the hypodermis. It comprises dense irregular connective tissue, as well as other structures such as hair follicles, blood vessels and other cellular structures. All of these structures are essential for the proper function of the skin, body and homeostasis. The dermis is an environment rich in collagen, fibrin, and elastin all of which give the skin many of its physical properties. Changes in abundance of these proteins may lead to poor appearance of the skin and these changes may be exacerbated by aging. The structure of the dermis is in the form of dermal papillae and function in part to support the overlying avascular epidermis. An underappreciated function of the dermis is the exchange of oxygen, nutrients, and the removal of waste products as well as promoting the physical characteristics of the skin. The dermis, therefore, is an important structure that functions in tandem with the epidermis.

Optimized, human embryonic fertility media including simplex optimized media may further be supplemented with additives or supplements with properties that stimulate molecular and physiological processes such as autophagy that allows for cells to replenish their substrate pool through the recycling of organelles and the removal of old free radicals and damaged proteins.

Biguanides are substances initially extracted from French lilacs and used in the treatment of hyperglycemic patients for hundreds of years. They are colorless solids, readily soluble in water. In solution, many biguanides hydrolyze to ammonia and urea prompting the development of more stable biguanide derivatives. Biguanides have a wide range of metabolic effects. Particularly important for the present invention, biguanides increase anaerobic glycolysis and, thus, decrease oxidative respiration and endogenous concentrations of harmful free-radicals.

Metformin and other biguanide derivatives act by activating the AMP activated protein kinase (AMPK) pathway via liver kinase B1 (LKB1). The AMPK pathway inhibits the mammalian target of rapamycin (mTOR) pathway. Inhibition of the mTOR pathway causes a reduction of protein synthesis and proliferation. Indirectly, metformin reduces protein kinase B (Akt) activation through phosphorylation of insulin receptor substrate-1 (IRS-1) (AMPK mediated), and, in turn, inhibits mTOR. To date, there are many non-biguanide substances whose mechanism of action relates to the inhibition of mTOR. Substances including, but not limited to, for example, apigenin, cryptotanshinone, fisetin, quercetin, galegine, and resveratrol are contemplated as potential substitutes or supplements in the preparation of the present invention Furthermore, examples of unexpected results are seen in patients taking metformin while undergoing chemo as well as radiotherapy. These patients do significantly better when compared to patients not taking metformin. The rationale for this phenomenon is attributed to, in part, metformin's effects via mTOR signaling. Such unexpected results may suggest that cancer patients may benefit from metformin.

Through their inhibition of mTOR, biguanides stimulate autophagy that allows for cells to replenish their substrate pool through the recycling of organelles and the removal of old free radicals and damaged proteins. Cells with limited access to a vascular supply lack sufficient substrates and cannot metabolically flourish due to limited resources. These cells inhibit mTOR mediated processes to undergo autophagy. The synergistic effect of biguanides and the attenuation of hypoxia is believed to stimulate the removal of old, oxidized proteins in the epidermis and stimulate their renewal and repair. RNA sequencing has shown that biguanides may shift the biological as well as metabolic profile of tissues to resemble younger tissues in terms of oxidative stress and substrate levels. Biguanides may achieve this by restoring the balance of autophagy and by decreasing endogenous oxidative stress. Therefore, biguanides exhibit anti-aging properties and may even reverse the process of aging.

The prior art and present cosmetic or medical interventions do not address the deficiencies previously described, and further fail to appreciate the significance of regulating the hypoxia microenvironment niches of the skin tissue in combination with optimal concentration of nutritional and energy substrates to stimulate molecular and physiological processes to promote tissue regeneration, anti-aging, and skin health.

BRIEF SUMMARY OF THE PRESENT INVENTION

In accordance with a preferred embodiment of the present invention, a modified, simplex optimized KSOMM-aa media combined with biguanide and/or functional equivalents to create the optimal microenvironment for the skin, or any other stem cell microenvironment. In yet another embodiment of the present invention, a dermatological preparation of the present invention which comprises optimal modified preimplantation fertility culture media such as Sydney IVF cleavage medium, Sydney IVF blastocyst medium, FERTICULT medium, FERTICULT G3, IVC-ONE, IVC-Two medium, Embryo Assist, Blast Assist, G-1 v5 Plus, G-2 v5 Plus, ECM medium, Multiblast Medium, Quinn's Advantage cleavage, or a one-step Global medium in combination with biguanide and/or functional equivalents. In yet another embodiment of the present invention, a dermatological preparation of the present invention which comprises optimal modified Assisted Reproductive Technology (ART) media used for andrology, ovum flushing, or freezing, wherein said ART media comprises ORIGIO Flushing Medium, SynVitro® Flush, Global® Collect®, Global® Total® LP w/HEPES, Global® Total® w/HEPES w/HAS, Universal IVF Medium, ORIGIO® Sequential Fert™ Quinn's Advantage™ Protein Plus Fert Medium, EmbryoGen®, or BlastGen™ in combination with biguanide and/or functional equivalents. The invention aims to promote tissue regeneration, anti-aging, and promote wound and bone healing.

The present invention utilizes the synergistic combination of nutrients, minerals, proteins derived and optimized from modified human fertility media in combination with biguanide and/or functional derivatives and/or other substrates in a formulation (La Secret Formula™) for use in skin care, hair care, or body care applications and other applications disclosed herein. Hereinafter the use of the terms "functional derivative" and "functional equivalent" are interchangeable, and its meaning is considered one and the same. The concentration of each of these substrates is optimized to yield the most efficient formulation. In one embodiment of the present invention, the topical application of the synergistic combination of modified human fertility media plus biguanides and/or functional derivatives. Examples of functional derivatives of biguanides may be derived from plant extracts which are contemplated in the present invention.

Early biguanide derivatives were extracted from French lilac Galega officinalis which were found to contain trace amounts of various biguanides such as galegine. In early medicine, French lilac extracts were prescribed for pre-diabetic and diabetic patients. It is now well known that biguanide drugs such as metformin have beneficial effects on glucose normalization with minimal risk of side-effects. In addition to French lilac, functional equivalents of biguanides may be derived from other plants such as goldenseal, goldthread and tree turmeric. In yet another example of a functional equivalent contemplated in the present invention includes compounds which inhibit mTOR activity and/or exhibit glucose normalizing properties such as Epigallocatechin Gallate (EGCG) which may be found in green tea, curcumin, caffeine, resveratrol, and genistein. The dermatological preparation of the present invention may comprise functional equivalents of biguanides derived from French lilac or other plant extracts as described herein to achieve anti-aging benefits via the mechanisms previously described. In yet another embodiment of the present invention, the formulation is specifically formulated to supplement tissues not dependent on oxidative respiration, and further decrease endogenous oxidative stress to produce anti-aging properties.

The present invention further targets the hypoxic microenvironment of the skin through modified human fertility media combined with biguanides or functional equivalents. In yet another embodiment of the present invention, important substrates used are L-Glutamine, Glycyl-Glutamine (GlyGln), and Alanyl-Glutamine (AlaGln). In yet another embodiment, the invention is specifically formulated to prevent nitrogen buildup. It is well known that glutamine dissociates in solution to form glutamic acid or poly-γ-glutamic acid and ammonia, causing nitrogen buildup. The use of a dipeptide such as glycyl-glutamine or alanyl-glutamine decreases this effect. The present invention further contemplates use of other glutamine stabilizing compounds including a tripeptide, a polypeptide, or a modified peptide. An advantageous working formulation of the present invention may contain ascorbic acid. The present invention, therefore, contemplates a means for stabilizing nitrogen containing labile compounds to prevent ammonia buildup.

In yet another embodiment of the present invention, a formulation comprises the use of modified human fertility culture media combined with biguanides and/or other substances and/or functional equivalents. These may be in topical, injectable or depot formulation. The applications of the present invention are for skin care, hair care, body care, dental procedures, and for regenerative medicine such as promoting wound and bone healing. Wound healing properties of the present inventions are not limited to external wounds. It is further contemplated that beneficial properties of the present invention exist for surgical procedures and bone healing. In yet another embodiment of the present invention, the formulation comprises modifications of the fertility culture media combined with biguanides and/or functional derivatives with other sub states that may promote or improve the desired effects.

The present invention further relates to a method for making, for example, modified, simplex optimized KSOMM-aa—human embryonic fertility media in combination with biguanide and/or functional derivatives and/or other substrates. The present invention further relates to a method for making optimized, modified one-step or two-step preimplantation fertility culture media comprising Sydney IVF cleavage medium, Sydney IVF blastocyst medium, FERTICULT medium, FERTICULT G3, IVC-ONE, IVC-Two medium, Embryo Assist, Blast Assist, G-1 v5 Plus, G-2 v5 Plus, ECM medium, Multiblast Medium, Quinn's Advantage cleavage, or a one-step Global medium in combination with biguanide and/or functional derivatives and/or other substrates. The present invention further relates to a method for making optimized, modified Assisted Reproductive Technology (ART) media comprising ORIGIO Flushing Medium, SynVitro® Flush, Global® Collect®, Global® Total® LP w/HEPES, Global® Total® w/HEPES w/HAS, Universal IVF Medium, ORIGIO® Sequential Fert™, Quinn's Advantage™ Protein Plus Fert Medium, Embryo-Gen®, or BlastGen™ in combination with biguanide and/or functional derivatives and/or other substrates.

As alluded to previously, it is known in the art that organs, tissues, and cells may be cultivated outside of their setting in situ but only if a suitable media containing an optimal composition of nutritional and energy substrates is properly formulated to meet the nutritional and energy requirements of each organ, tissue, or cell. The nutritional and energy requirements for one cell type, tissue type, or organ are distinct and differs from that of another. Specifically, it is known in the art that the nutritional requirements of preimplantation embryos are distinct and differs from those of adult somatic cells. Furthermore, early embryos show an evolving requirement for energy substrates as the embryos mature into blastocysts, preferring pyruvate-lactate while the embryos are under maternal genetic control and preferring glucose-based metabolism after activation of the embryonic genome.

A preferred embodiment of the present invention comprises a method for making modified human embryonic fertility media suitable for the microenvironment niches of the skin tissue as well as the microenvironment niches of existing—in the case of skin tissue—stem cells in the *stratum basale* layer.

While the present invention is discussed with respect to the modified, simplex optimized, human fertility media or modified one-step or two-step preimplantation fertility culture media or modified ART media combined with biguanide and/or functional equivalents (LaSecret Formula) and the method for making same, it is understood and appreciated by those skilled in the art that the present invention also discloses an advantage over the prior art in at least three respects: (1) it is specially formulated to target the hypoxic microenvironment niches of the skin tissue in combination with optimal concentration of nutrients, ions and minerals; (2) it is specially formulated to stimulate existing stem cells to trigger the capacity of stem cells to divide and renew and differentiate into specialized cells; and (3) it is specially formulated to stimulate molecular and physiological processes, e.g., autophagy, to replenish the substrate pool through the recycling of organelles and the recycling of old damaged proteins and countering free-radical damage.

BRIEF DESCRIPTION OF THE DRAWINGS

Preferred exemplary embodiments of the present invention are illustrated in the accompanying drawings, in which liked reference numerals, if any, represent like parts throughout, and in which:

FIG. 1 is an advantageous working formulation of the present invention showing suitable composition of optimized, modified human embryonic fertility media.

FIG. 2 is an advantageous working formulation of the present invention showing optimized composition of modified human embryonic fertility media in combination with biguanide. (LaSecret Formula™)

FIG. 3 is an advantageous working formulation of the invention in a cream form.

FIG. 4 is an advantageous working formulation of the invention in a gel form.

FIG. 5 is an advantageous working formulation of the invention in an eye cream form for application on the external skin.

FIG. 6 is an advantageous working formulation of the invention in a hydrogel form.

FIG. 7 is an advantageous working formulation of the invention in a spray mist form.

FIG. 8 is an advantageous working formulation of the invention in a shampoo.

FIG. 9 is an advantageous working formulation of the invention in a hair conditioner.

FIG. 10 is an advantageous working formulation of the invention in a face mask.

FIG. 11 is an advantageous working formulation of the invention in an antiseptic hand spray.

FIG. 12 is an advantageous working formulation of the invention in a mesotherapy.

FIG. 16 is an exemplary, schematic flow chart of the method for making optimized, modified human embryonic fertility media.

DETAILED DESCRIPTION OF A PREFERRED EMBODIMENT

Figure 13:
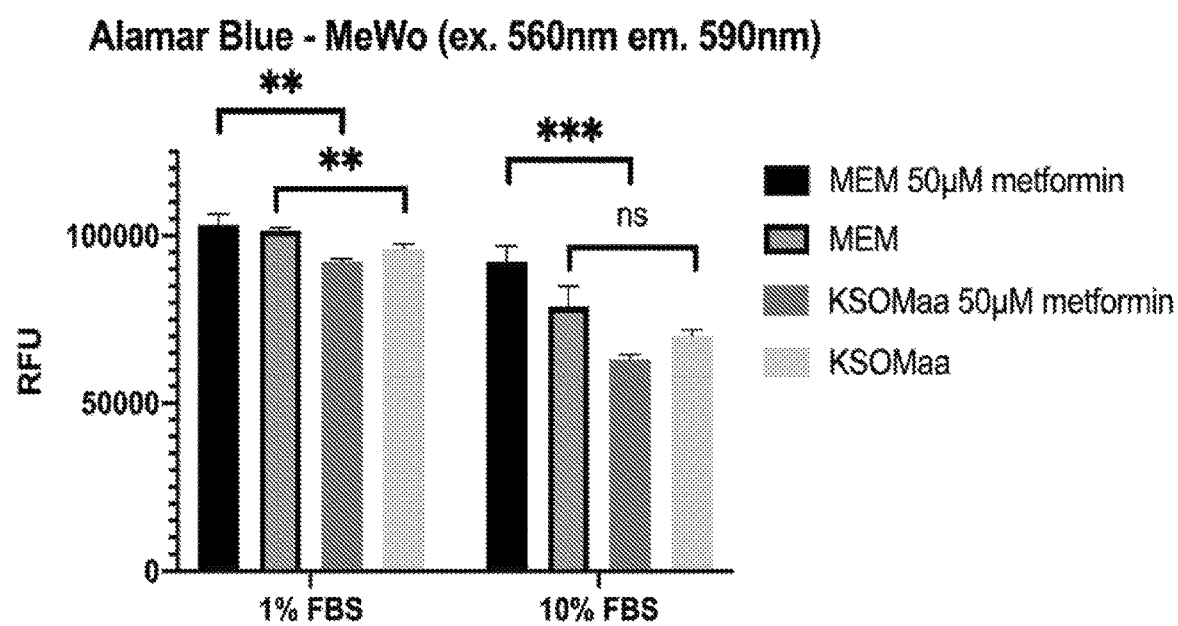
FIG. 13 is a graph representing the effects of the present invention on the metabolic activity/viability of MeWo cells.

Simplex optimization as applied to fertility medicine is an algorithm that allows for the determination of optimal substrate concentrations with the endpoint of yielding the highest number of zygote to blastocyst events. It is an efficient method for optimizing culture media by allowing the optimization of many variables simultaneously. The formulation of the present invention described herein contains substrate concentrations that are simplex optimized to support the stem cell phenotype and stem cell metabolism as well as target the hypoxic microenvironment niches of skin tissue.

As shown in FIG. 1 and FIG. 2, the advantageous working formulation of the invention relates to an optimized, modified human fertility culture media combined with biguanides (LaSecret Formula™) for anti-aging and renewal properties. The formulation of the present invention is free from any microbial or other contamination. Use of the invention may be incorporated into a wide range of applications including, but not limited to, the cosmetic industry or tissue regeneration such as wound repair or bone healing. A method for making an optimized, modified human fertility culture media combined with biguanides (LaSecret Formula™) is further described herein, As shown in FIG. 3, FIG. 4, FIG. 5, FIG. 6, and FIG. 7, the advantageous working formulation of the invention may be prepared as part topical cream, gel, eye cream, hydrogel, or spray mist, respectively. Further, topical cream, sera, and pre-soaked mask of the invention may be used as part of the water phase in the form of an emulsion, suspension, solution, or gel, as shown in, for example, FIG. 3, FIG. 4, FIG. 5, FIG. 6 and FIG. 10. The formulation may further be prepared as a "ready-mixed" product that may be pre-mixed just prior to application such as in powder, granules, or concentrate syrup form for use, for example, on the epidermis, dermis, or other parts of the human body.

In yet another embodiment, the present invention may be in the form of a cosmetic product mixed with other substances to achieve the desired properties and the desired result. For instances, substances may be used to modulate texture or moisture or other properties of the product to achieve the desired result. The invention may be modified further to alter pH and/or osmolarity.

It is further contemplated that formulation of the present invention may be in a concentrate form such that it is incorporated as part of a solution, wherein the final diluted concentration of the substrates will be maintained, and the final concentrations are substantially similar and functionally equivalent to those illustrated in FIG. 1 and FIG. 2.

A person skilled in the art will appreciate that the formulation of the present invention may be prepared and incorporated into a variety of products. A preferred embodiment of the present invention is the preparation of the invention as part of a water base product. However, the formulation of the invention may be used as part of an emulsion (Oil/Water, Water/Oil, Water/Oil/Water), suspension, solution, or gel of any known defined or undefined medium, as shown in, for example, the advantageous working embodiments described herein.

Further, an embodiment of the invention may be used as part of mesotherapy in the form of dermal microinjections or infusions. In this regard, the present invention may be used in combination with other substances such as Argireline (acetyl hexapeptide-8) to achieve the desired result as shown in, for example, FIG. 12.

In yet another embodiment of the invention, a preparation may be applied to the scalp in the form of a shampoo, conditioner, hair mask, or scalp mask as shown in, for example, FIG. 8, FIG. 9, and FIG. 10.

The formulation of the present invention may also be used to promote wound healing. Wound healing applications may be in the form of pre-soaked bandages, dressings, gauze or cleansing solutions. The formulation of the invention may further be used during surgery and may be incorporated—for example—in the form of surgical glue to accelerate wound healing.

In yet another embodiment of the invention, the formulation may further be incorporated into other products including, but not limited to, surgical sutures, staples, or diffusing beads that may be pre-treated with a desired preparation of the present invention—for example, a dehydrated powder preparation of the invention. In the case of bone fractures, the formulation of the invention may be incorporated into metal plates to accelerate healing and reduce the risk of surgical complications.

In yet another embodiment of the invention, the formulation of the present invention may be further used in combination with an antibacterial or antiviral or antifungal agent for application as a skin cleanser as shown in the advantageous working formulation of FIG. 11.

In another embodiment, the formulation of the present invention may be incorporated into a pharmaceutically appropriate carrier or other excipients to achieve the desired bioavailability of the active ingredient. More recently, novel drug delivery systems have changed the landscape of the kinds of molecules that can be transported across cell membranes. For instance, liposomal, nanoparticle, and receptor tagged substances have been shown to increase drug, or substrate delivery and these delivery systems are contemplated in the present invention and may be incorporated to optimize a given formulation of the present invention.

Another embodiment of the present invention may also be used to prevent hair loss, and/or greying or hair discoloration and/or to stimulate hair growth as shown in the advantageous working formulation of FIG. 8 and FIG. 9.

Another preferred embodiment of the present invention, a formulation of the invention prepared for topical administration to deliver transdermal nourishment and anti-aging substances to the skin tissue, as shown in, for example, the advantageous working embodiments described herein.

In another embodiment of the invention, formulation of the invention may be prepared to yield a product suitable for topical eye administration, as shown in the advantageous working formulation of FIG. 5.

The formulation of the invention may also be prepared in a stable lipid, micelle, liposome, and/or nanoparticle. A person skilled in the art will further appreciate that the formulation of the present invention may be used in combination with substances derived from plants, biological or marine extracts including, but not limited to, peptides, vitamins, emulsifiers, and other minerals or substrates.

As previously stated, the present invention discloses an advantage over the prior art in at least three respects. For instance, a preferred embodiment of the present invention is specially formulated as disclosed in the advantageous working formulation described herein to stimulate molecular and physiological processes such as, but not limited to, cell migration, cell survival, and cell proliferation and thereby demonstrating anti-aging activity and wound healing properties.

It is well known in the art that metformin is a biguanide antidiabetic medication that activates the adenosine monophosphate-activate protein kinase (AMPK) pathway and, consequently, inhibits the mammalian target of rapamycin (mTOR) signaling cascade. Metformin further inhibits the respiratory chain complex I in the mitochondria which, in turn, suppresses oxidative phosphorylation. A gross physiological effect is the normalization of blood glucose. High blood-glucose is a known risk factor in the development or cardiovascular disease, stroke and cancer which are the leading causes of death in the developed world. The effects of metformin on cell migration, survival, and proliferation may explain why patients taking metformin live longer or may further explain why old tissues treated with metformin have a similar genetic and proteomic profile as untreated young tissues. It is further known in the art that metformin may regulate metabolism by activating molecular pathways related to low food abundance and hence may decrease cell division. It is further known in the art that decreased cell division due to metformin may be rescued by the presence of Glutamine as an alternative source of fuel instead of glucose. This phenomenon is supported by evidence that glutaminase inhibitors restore the cytostatic phenotype. Since a preferred embodiment of the present invention comprises L-glutamine and Glycyl-Glutamine, cells cultured in an advantageous working formulation of the invention may exhibit decreased cellular metabolism or may show no change in metabolic activity relative to cells cultured in control media (MEM 50 μM metformin) depending on the cellular energy needs.

For example, as shown in FIG. 13, the advantageous working formulation of the present invention (hereinafter also referred to as KSOMaa 50 μM metformin) is simplex optimized, modified human embryonic fertility media in combination with metformin to normalize blood glucose levels to modulate the metabolic process and, thereby, control the aging process. To demonstrate the effects of the present invention on metabolic viability of cells, an Alamar Blue Assay was performed using a protocol known to those skilled in the relevant art to measure the metabolic viability of MeWo cells cultured in Potassium Simplex Optimized Medium supplemented with essential and non-essential amino acids (KSOMaa) with 50 μM metformin or in KSOMaa alone, or cultured in control media (MEM) with and without 50 μM metformin. Those skilled in the art would appreciate that MeWo is a human derived cell line that exhibits a fibroblast morphology with a robust adhesion property that makes this cell line suitable for in vitro experiments.

As shown in FIG. 13, the metabolic activity/viability of MeWo cells was decreased when cultured in KSOMaa 50 μM metformin relative to cells cultured in control media (MEM 50 μM metformin). Specifically, under starvation conditions (1% FBS), the metabolic activity of MeWo cells cultured in control media (MEM 50 uM metformin) is 10% () higher relative to cells cultured in KSOMaa 50 μM metformin. Under high serum conditions (10% FBS), the metabolic activity in cells cultured in MEM 50 μM metformin is 32% (*) higher relative to cells cultured in KSOMaa 50 μM metformin. The decreased metabolic activity of MeWo cells cultured in KSOMaa relative to cells cultured in control media (MEM) demonstrates the anti-aging effects of simplex optimized, modified human embryonic fertility culture media of the present invention since decreased metabolism is correlated with decreased intrinsic aging.

The results shown in FIG. 13 is further explained by the novel composition of optimized, modified human embryonic fertility culture media of the present invention which is specially formulated to support the transition of zygote to blastocyst prior to host reimplantation thereby increasing the probability of implantation and ultimately the development of a viable human embryo. In contrast, the control media (MEM), including other known and common tissue culture media, lack the novel composition of the optimized, modified human embryonic fertility culture medium of the present invention. Specifically, the control media (MEM) is formulated to support the amplification of neoplastic cells such as, for example, HeLa cells, HEK 293 cells, CHO cells, or other neoplastic cells in culture in a petri dish rather than to support the development of an viable embryo in the human body. The applicant, therefore, contends that the novel composition of optimized, modified human embryonic fertility media of the present invention is far superior to common tissue culture media for application in skin care, hair care, body care, dental procedures, and for anti-aging and regenerative medicine such as promoting wound or bone healing.

In addition to its effects on cell metabolism, the advantageous working formulation of the present invention also regulates cell proliferation and decrease cell death relative to the effects of control media. The applicant contends that cells cultured in the advantageous working formulation of the present invention will exhibit superior cell or protein content. Greater cell number or protein content may result from either an increase in mitotic rate, or a decrease in cell death with a steady mitotic rate, or some degree of both. As disclosed in the experimental results of FIG. 13, since MeWo cells cultured in the advantageous working formulation of the present invention (KSOMaa 50 μM metformin) showed a decreased metabolism, it stands to reason that an increase in cell number or protein content would not result from an increased mitosis rate. To further test the beneficial properties of a preferred embodiment of the present invention, a Sultorhodamine B (SRB) study was conducted to determine cell survival and cytotoxicity as a measure of absolute protein content that is related to cell number.

Figure 14:
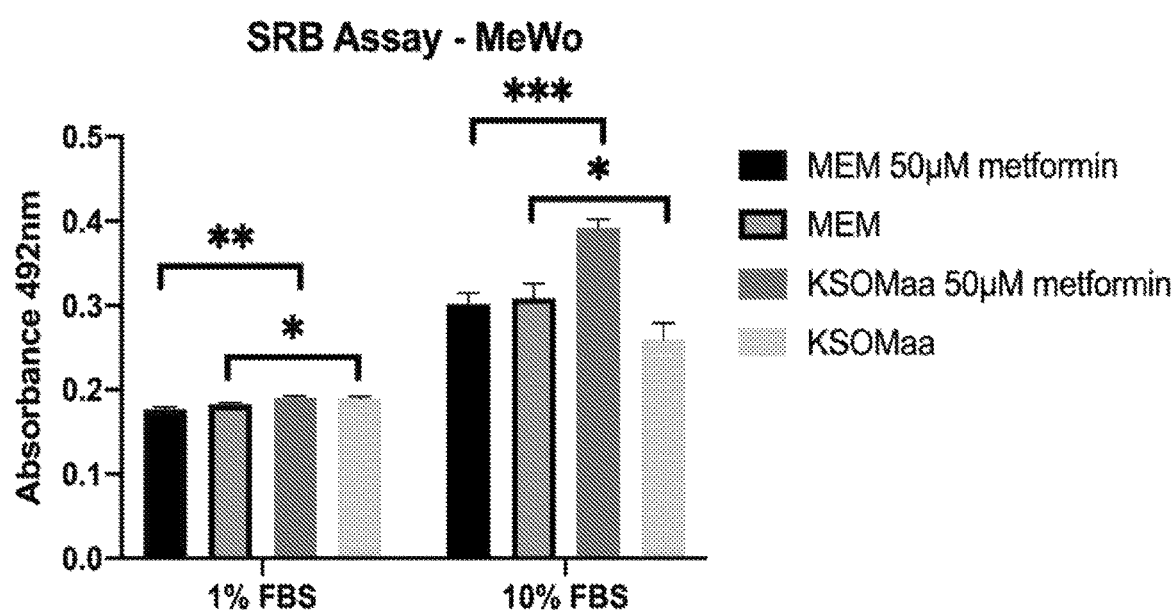
FIG. 14 is a graph representing the effects of the present invention on cell survival of MeWo cells.

As shown in FIG. 14, and consistent with the anti-aging properties of the present invention, the protein content or cell number of MeWo cells was significantly higher when cells were cultured in an advantageous working formulation of the present invention (KSOMaa 50 μM metformin) as compared to cells cultured in control media (MEM 50 μM metformin). Specifically, MeWo cells cultured in the working formulation of the present invention showed an approximately 30%(***) increase in cell number relative to cells cultured in control media MEM+/−50 μM metformin, thereby demonstrating the beneficial effects of the preferred embodiment of the present invention on cell proliferation and its anti-aging properties. As described herein, the SRB study is an indicator of protein abundance from live cells and thus correlates with relative cell number between experimental conditions. Since simplex optimized, modified human embryonic fertility culture media with 50 μM metformin of the present invention does not increase cell metabolism, the effects shown in FIG. 14 suggest that cells cultured in the working formulation of the present invention live longer and are better equipped to proliferate to achieve a net effect of increased protein content. In the context of regenerative medicine, the increase in overall cell number and protein content is thought to support de novo collagen synthesis with limited loss. Accordingly, the applicant contends that the simplex optimized, modified human embryonic fertility culture media in combination with biguanide of the present invention is superior to the existing art.

Figure 15A:
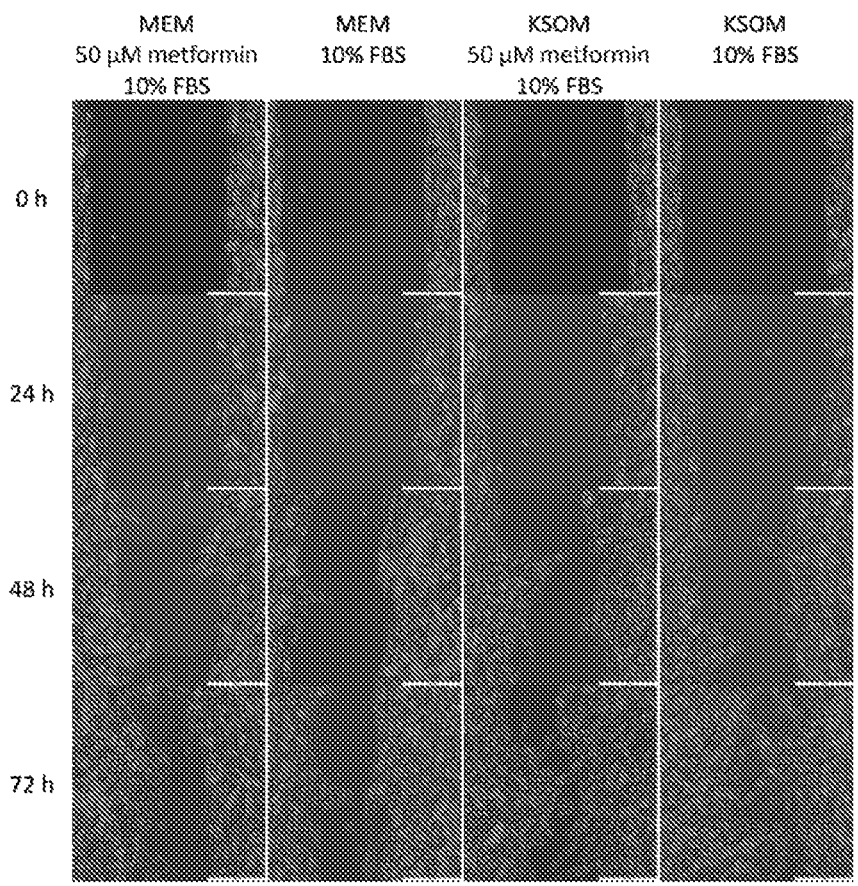
FIG. 15a and FIG. 15b represent the effects of the present invention on cellular migration and wound healing of MeWo cells
Figure 15B:
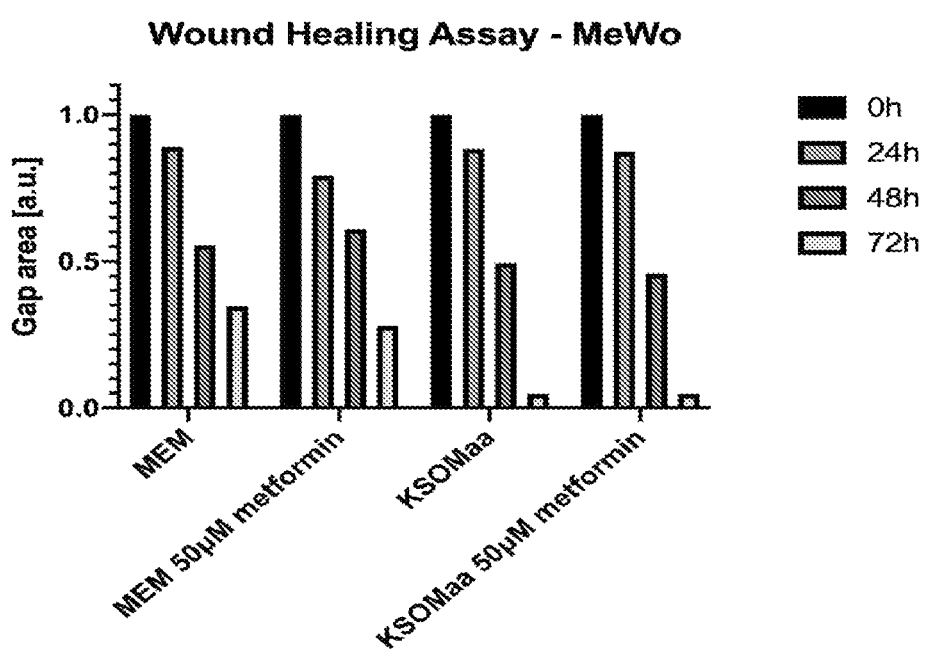

To further demonstrate an advantage of the present invention over the prior art, a wound healing study was conducted using the advantageous working formulation of the present invention and MeWo cells. As shown in FIG. 15a and FIG. 15b, and consistent with the regenerative properties of the present invention, a functional assessment of molecular and physiological processes of MeWo cells cultured in KSOMaa 50 µM metformin or cultured in KSOMaa alone demonstrates a higher wound closure when compared to cells cultured in control media (MEM+/−50 µM metformin). Microscopy images as shown in FIG. 15a depict the wound closure over time as measured at t=0, 24, 48, and 72 hours. As shown in FIG. 15b, the wound closure is represented in a graph quantified as the area of the wound ("gap") at each time reference plotted as a ratio of said area and the initial area at t=0.

Accordingly, the data demonstrates that cells cultured in an advantageous working formulation of the present invention are induced in a time-dependent manner to migrate and close the "gap" to promote wound healing. Consistent with this effect and, as shown in FIG. 15a, it may be qualitatively observed that cells cultured in KSOMaa demonstrate significantly increased podocyte extension which is consistent with cell migration into the direction of wound opening, i.e., a closing of the gap. This qualitative observation suggest that the beneficial effects of the present invention is derived from the novel composition found in simplex optimized modified human embryonic fertility media of the present invention. Therefore, the applicant contends that an advantage of the present invention over the prior art includes the stimulation of essential molecular and physiological processes leading to cell migration, cell survival, and cell proliferation and, thereby, demonstrating anti-aging activity and wound healing.

In yet another advantage over the prior art, a preferred embodiment of the present invention is specially formulated as disclosed in the advantageous working formulation described herein to target the hypoxic microenvironment niches of the skin tissue in combination with optimal concentration of nutrients, ions, and minerals. A monolayer of cell culture is a useful in vitro scientific model to study basic cell behavior and molecular processes. However, a monolayer of cell culture is an unreliable model to study in vivo phenomena such as understanding the dynamic microenvironment present in tissues and organs. The dynamic microenvironment results in part from gradients in oxygen levels, substrates, and other metabolites. For example, normoxic cells directly adjacent to an oxygen source may produce ATP via oxidative phosphorylation and glucose. In contrast, hypoxic cells will produce ATP via glycolysis and the incorporation of L-Glutamine into the Krebs's cycle; consequently, decreasing the microenvironment pH and increasing lactic acid production in hypoxic tissue regions.

One approach to partly overcome the limitations of the in vitro monolayer culture is to develop a working model of the dynamic microenvironment of multicellular tissue through spheroid formation. Spheroids are spherical clumps of cells grown on a non-adhesive medium such as agar. It is well known in the art that cells located within the core of a spheroid are in a hypoxic microenvironment. Various culture conditions aimed at alleviating or normalizing hypoxia may be measured using a nitroimidazole compound called EF5. Standard assays and protocols known in the art have been developed to stain for EF5 using immunohistochemistry or immunofluorescence. MeWo cells have the capacity to form spheroids when grown under controlled culture conditions in a non-adhesive medium such as agar. The MeWo spheroids may then be stained for EF5 to assess the level of hypoxia. The advantageous working formulation of the present invention, for example, but not limited to, KSOMaa 50 µM metformin, is specially formulated to decrease EF5 staining which is indicative of decrease hypoxia in MeWo spheroids.

In yet another advantage over the prior art, a preferred embodiment of the present invention is specially formulated as disclosed in the advantageous working formulation described herein to stimulate existing stem cells to divide, renew and differentiate into specialized cells. Within the deepest layer of the skin, S basale of the epidermis, actively dividing and differentiating stem cells lead to improved tissue architecture of skin, improved skin morphology, collagen density, and many other markers of healthy skin such as moisture content. In vivo reflective confocal microscopy is a known procedure for assessing the 3-Dimensional structure of human skin including tissue architecture, morphology, collagen density, and moisture content. It is a preferred means for examining the health of human skin due to the observable depth of tissue penetration.

A preferred embodiment of the present invention is specially formulated to promote healthy skin moisture content as well as long-term improvement of collagen density, tissue architecture, and morphology of the skin. The beneficial effects of the present invention may be observed using in vivo reflective confocal microscopy. As disclosed in FIG. 13, FIG. 14, FIG. 15a, and FIG. 15b, a preferred embodiment of the present invention demonstrates the capacity to stimulate essential molecular and physiological processes leading to cell migration, cell survival, and cell proliferation and, thereby, demonstrating anti-aging activity and wound healing. Consistent with the experimental results disclosed herein, a topical formulation of the present invention is specially formulated to promote healthy human skin.

To further promote healthy human skin, a preferred embodiment of the present invention is formulated to stimulate the stress-coping mechanisms of skin cells and inhibit cell apoptosis. Aging cells are under stress which, in turn, trigger changes in the expression of essential genes involved in the cellular-stress response such as apoptosis, or autophagy/unfolded protein response. A preferred embodiment of the present invention is formulated to modulate gene expression of essential genes involved in the cellular-stress response, which may be assessed and quantified using reverse transcribed quantitative polymerase chain reaction (RT-qPCR) and SYBR-green. For instance, a preferred embodiment of the present invention is formulated to decrease the gene expression of genes involved in apoptosis such as BCL2 and CASP3, or to decrease the gene expression of genes implicated in autophagy/unfolded protein response such as BIP, CHOP, XBP1. A full panel of related transcripts may be measured such as BIP, CHOP, XBP1, BCL2, CASP3, GADD45a, IGFBP2, HIF1a, CDKN1A, TP53, GAPDH, and RN18S1.

In addition, a preferred embodiment of the present invention is formulated to not only modulate gene expression but also to affect the protein expression of essential proteins involved in the cellular-stress response. It is well known in the art that immunofluorescence is a preferred means to assess the intracellular organelles and cellular markers induced as a result of stress or autophagy on a per cell basis. Under stress conditions, cells up-regulate various pathways such as the unfolded protein response (UPR) or autophagy which may lead to intracellular degradation of organelles and changes in lysosomal number (Mannose-6-phosphatereceptor) as well as endosomes (early endosome antigen 1). Cells undergoing autophagy demonstrate changes in punctate fluorescence corresponding to M6PR tagged lysosomes in the cytoplasm. A preferred embodiment of the present invention is formulated to down-regulate and inhibit the various pathways leading to intracellular degradation including decreased lysosomal vacuoles and endosomes. The applicant, therefore, contends that an advantage of the present invention over the prior art includes targeting the hypoxic microenvironment of the skin and stimulating existing stem cells to divide, renew, and differentiate to promote healthy skin.

In another preferred embodiment of the present invention, a method for making optimized, modified human embryonic fertility media is disclosed as shown in, for example, FIG. 16.

A method comprising the steps: (a) defining a start and target location; (b) selecting and defining a first media, "START" simplex, that has been shown to be safe and effective, wherein said first media is KSOM, one-step or two-step preimplantation fertility culture media, or Assisted Reproductive Technology (ART) media. The one-step or two-step preimplantation media comprising Sydney IVF cleavage medium, Sydney IVF blastocyst medium, FERTICULT medium, FERTICULT G3, IVC-ONE, IVC-Two medium, Embryo Assist, Blast Assist, G-1 v5 Plus, G-2 v5 Plus, ECM medium, Multiblast Medium, Quinn's Advantage cleavage, or a one-step Global® medium. The ART media comprising ORIGIO Flushing Medium, SynVitro® Flush, Global® Collect®, Global® Total® LP w/HEPES, Global® Total® w/HEPES w/HAS, Universal IVF Medium, ORIGIO® Sequential Fert™, Quinn's Advantage™ Protein Plus Fert Medium, EmbryoGen®, or BlastGen™; (c) identifying the composition of said first media including osmolarity, pH, nutrients, preservatives, and energy substrates, e.g., glucose and TCA intermediates to thoroughly understand the role that each substrate composition plays including, for example, whether it is to provide a carbon-source, a co-factor, pH regulator, or as an osmotic agent; if necessary, further (d) dissecting the composition into essential and non-essential substances. Whether a substance is essential depends on the preparation and application; (e) selecting a "TARGET location", e.g., skin tissue; (f) identifying the specific characteristics of the microenvironment niche of the TARGET location which will dictate the final formulation. Key parameters include osmolarity, pH, presence of commensal and non-commensal microorganisms, oxygenation, blood perfusion, presence of immune system cells and other physiological characteristics. The identified target components for optimization in the new media may be oxygenation, fluid-loss, hypo/hyper-thermia, substrates such as essential and non-essential amino acids, lipid profiles, other substrates such as EDTA, Pyruvate, $KH_2PO_4$, Glucose, cytokines, proteins, peptides, electrolytes and other desirable components.

Once key characteristics are identified in the target location, they are divided between essential and non-essential substances ((g) dissecting the TARGET location). Again, whether a substance is essential depends on the preparation and application. A comparison between the START and TARGET location essential and non-essential components is accounted for during the first cycle of media modification ((h) Cross Comparing the START and TARGET). The preparation is further optimized to limit and preferably to eliminate any substrate-substrate interactions which may result in one substrate exhibiting countervailing properties of another. These interactions are synonymous to drug-drug interactions in pharmacology where the presence of one drug may alter the therapeutic effects of another. Additional cycles of media modification and optimization may be necessary depending on the START simplex and TARGET location.

Objective tests, well known to a person skilled in the art, may be performed to assess the effectiveness of the optimized preparation through its formulation into, for example, a topical cream and the effects of said cream maybe measured through in vivo reflexive confocal microscopy to assess the altered refractive index of the epidermis (skin hydration), or during more extended studies, the effects of said cream on collagen may be measured.

The method of the present invention is iterative (Steps (i) and (j)) and a few cycles of optimization of the START simplex to reflect the needs of the TARGET location may be necessary to produce a desired product, e.g., See FIG. 16.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above descriptions then, it is to be realized that the present invention including the optimum steps and the optimum sequence of steps of the invention to include variations in media composition (i.e., substrates) as well as media conditions—depending on its intended application—are deemed readily apparent and obvious to one skilled in the art, and all equivalent relationships to those illustrated in the drawings and described in the specifications are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modification and equivalents may be resorted to, falling within the scope of the invention.

The invention claimed is:

1. A dermatological preparation comprising a simplex-optimized human embryonic fertility medium and biguanide or biguanide derivative wherein the preparation is an oil-in-water formulation for application for skin care, hair care, body care, dental procedures, anti-aging, and regenerative medicine.

2. The dermatological preparation of claim 1, wherein the simplex-optimized human embryonic fertility medium is KSOMMaa medium.

3. The dermatological preparation of claim 1, wherein the simplex-optimized human embryonic fertility medium is preimplantation fertility culture media.

4. The dermatological preparation of claim 1, wherein the optimized modified simplex-optimized human embryonic fertility medium is Assisted Reproductive Technology media.

5. The dermatological preparation of claim 1, wherein the simplex-optimized human embryonic fertility medium comprises a combination of the following components in the following concentration ranges in g/L:

| | | |
|---|---|---|
| NaCl | 4.44 | 11.1 |
| KCl | 0.152 | 0.38 |
| KH2PO4 | 0.04 | 0.1 |
| MgSO4•7H2O | 0.04 | 0.1 |
| Glucose | 0.032 | 0.08 |

-continued

| | | |
|---|---|---|
| Sodium lactate | 0.896 | 2.24 |
| NaHCO3 | 1.68 | 4.2 |
| Sodium pyruvate | 0.016 | 0.04 |
| CaCl2•2H2O | 0.02 | 0.05 |
| EDTA | 0.0032 | 0.008 |
| Glycyl-glutamine | 0.1168 | 0.292 |
| L-Glutamine | 0.008 | 0.02 |
| L-Alanine | 0.0036 | 0.009 |
| Glycine | 0.003 | 0.0075 |
| L-Arginine | 0.05056 | 0.1264 |
| L-Asparagine | 0.006 | 0.015 |
| L-Aspartic Acid | 0.005328 | 0.01332 |
| L-Cystine | 0.009616 | 0.02404 |
| L-Histidine | 0.016768 | 0.04192 |
| L-Isoleucine | 0.020984 | 0.05246 |
| L-Leucine | 0.020992 | 0.05248 |
| L-Lysine | 0.029216 | 0.07304 |
| L-Methionine | 0.005968 | 0.01492 |
| L-Phenylalanine | 0.013216 | 0.03304 |
| L-Proline | 0.004608 | 0.01152 |
| L-Serine | 0.004208 | 0.01052 |
| L-Tryptophan | 0.004088 | 0.01022 |
| L-Tyrosine | 0.014496 | 0.03624 |
| L-Valine | 0.018736 | 0.04684. |

6. The dermatological preparation of claim 1, wherein the biguanide or biguanide derivative has a final concentration range of 0.001 g/L-10.0 g/L.

7. The dermatological preparation of claim 5, wherein the biguanide or biguanide derivative has a final concentration range of 0.001 g/L-10.0 g/L.

8. The dermatological preparation of claim 1, wherein the biguanide or biguanide derivative is of plant origin.

9. The dermatological preparation of claim 1, wherein the biguanide or biguanide derivative is a compound which inhibits mTOR activity or exhibits glucose normalizing properties.

10. The dermatological preparation of claim 1, wherein the biguanide derivative is Epigallocatechin Gallate.

11. The dermatological preparation of claim 1, wherein the preparation comprises glutamine stabilizing compounds.

12. The dermatological preparation of claim 5, wherein the preparation further comprises a dipeptide, tripeptide, or polypeptide, or modified peptide.

13. The dermatological preparation of claim 12, wherein the dipeptide is alanyl-glutamine.

14. The dermatological preparation of claim 1, wherein the preparation comprises ascorbic acid or derivatives thereof.

15. The dermatological preparation of claim 1, wherein the preparation is present as a microemulsion.

16. The dermatological preparation of claim 1, wherein the preparation is an oil-in-water formulation that is in the form of dermal microinjections or dermal infusions.

17. The dermatological preparation of claim 1, wherein the preparation—further comprises short peptides, DNA sequences, RNA sequences, modified peptides, modified DNA sequences, or modified RNA sequences.

18. The dermatological preparation of claim 1, wherein the preparation—further comprises acetyl hexapeptide-8.

19. The dermatological preparation of claim 1, wherein the preparation is a shampoo, a conditioner, a hair mask, or a scalp mask.

20. A method for making the dermatological preparation of claim 1, comprising mixing the simplex-optimized human embryonic fertility medium with the biguanide or biguanide derivative, and oil, thereby forming an oil-in-water formulation.

21. The dermatological preparation of claim 1, wherein the regenerative medicine is for wound or bone healing.

22. The dermatological preparation of claim 1, wherein the biguanide derivative is metformin.

23. The dermatological preparation of claim 5, wherein the biguanide derivative is metformin.

24. The dermatological preparation of claim 5, wherein the biguanide derivative is Epigallocatechin Gallate.

25. The dermatological preparation of claim 1, wherein the preparation further comprises a dipeptide, tripeptide, or polypeptide, or modified peptide.

\* \* \* \* \*